United States Patent
Franke et al.

(10) Patent No.: US 11,320,499 B2
(45) Date of Patent: May 3, 2022

(54) MAGNET ARRANGEMENT FOR GENERATING A SELECTION MAGNETIC FIELD, APPARATUS WITH A MAGNET ARRANGEMENT AND METHOD FOR GENERATING A SELECTION MAGNETIC FIELD

(71) Applicant: Bruker BioSpin MRI GmbH, Ettlingen (DE)

(72) Inventors: Jochen Franke, Karlsruhe (DE); Volker Niemann, Ispringen (DE)

( * ) Notice: Subject to any disclaimer, the term of this patent is extended or adjusted under 35 U.S.C. 154(b) by 0 days.

(21) Appl. No.: 17/482,929

(22) Filed: Sep. 23, 2021

(65) Prior Publication Data
US 2022/0091199 A1    Mar. 24, 2022

(30) Foreign Application Priority Data
Sep. 23, 2020 (DE) .................. 10 2020 211 948.1

(51) Int. Cl.
*G01R 33/12* (2006.01)
(52) U.S. Cl.
CPC ................................ *G01R 33/1276* (2013.01)
(58) Field of Classification Search
CPC .... G01R 33/1276; G01R 33/00; G01R 33/10; G01R 33/1269; G01R 33/0213; G01N 27/72; A61B 5/05; A61B 5/0515; A61B 5/7257
See application file for complete search history.

(56) References Cited

U.S. PATENT DOCUMENTS

2016/0216355 A1* 7/2016 Rahmer ............. G01R 33/1276

FOREIGN PATENT DOCUMENTS

| WO | 2011021165 A1 | 2/2011 |
|---|---|---|
| WO | 2018013731 A1 | 1/2018 |

OTHER PUBLICATIONS

Gaël Bringout, Field Free Line Magnetic Particle Imaging—Characterisation and imaging device up-scaling, Doctoral Dissertation, University of Lübeck, 2016 (Year: 2016).*
Knopp et al., Efficient generation of a magnetic field-free line, Med. Phys. 37 (7), pp. 3538-3540, 2010 (Year: 2010).*
Goodwill et al., Projection X-Space Magnetic Particle Imaging, IEEE Trans Med Imaging 31(5), pp. 1076-1085, 2012 (Year: 2012).*

* cited by examiner

*Primary Examiner* — Daniel R Miller
(74) *Attorney, Agent, or Firm* — Benoit & Côté Inc.

(57) ABSTRACT

A magnet arrangement for generating a selection magnetic field with a gradient and a field-free region in a sample volume includes: a Maxwell magnet system with two ring magnets, which are arranged in coaxial fashion and at a distance from one another on a common Z-axis extending through the sample volume, a focus field coil arrangement with at least one focus field coil pair for displacing the field-free region within the sample volume, and a drive coil for generating an MPI drive field. The magnet arrangement comprises a quadrupole magnet system with at least one quadrupole ring for generating a quadrupole magnetic field, the quadrupole magnet system being arranged coaxially with respect to the Maxwell magnet system. Using the magnet arrangement according to the invention, it is possible to switch between a selection magnet field with a field-free point and a field-free line without undesirably increasing the field gradient.

14 Claims, 17 Drawing Sheets

MAGNET ARRANGEMENT FOR GENERATING A SELECTION MAGNETIC FIELD, APPARATUS WITH A MAGNET ARRANGEMENT AND METHOD FOR GENERATING A SELECTION MAGNETIC FIELD

BACKGROUND OF THE INVENTION

Field of the Invention

The invention relates to a magnet arrangement for generating a selection magnetic field with a gradient B1 and a field-free region in a sample volume, the magnet arrangement comprising: a Maxwell magnet system with two ring magnets, which are arranged in coaxial fashion and at a distance from one another on a common Z-axis which extends through the sample volume, a focus field coil arrangement with at least one focus field coil pair for displacing the field-free region within the sample volume, and a drive coil for generating an MPI drive field, The invention also relates to a method for generating a selection magnetic field with a gradient B1 and a field-free region in a sample volume. Such a magnet arrangement is known from patent document WO 2011/021165 A1.

Description of the Related Art

By way of example, selection magnetic fields are used to magnetic particle imaging (MPI) methods, in which local concentrations of magnetizable nanoparticles (in particular superparamagnetic iron oxide nanoparticles—SPION) are ascertained in the interior of an object. These nanoparticles are periodically magnetized by an MPI drive field that is periodically varied at a predetermined frequency. For the spatial resolution, the drive field is superposed with a time-constant selection magnetic field which has a field-free region. Proceeding from this field-free region, the selection magnetic field increases quickly, and so the magnetizable particles already reach magnetic saturation at a small distance from the field-free region. Therefore, the MPI measurement signal originates from the local surroundings of the field-free region and provides information about the local particle concentration present there. Thus, a magnetic field with a gradient B1 (first-order gradient strength) and a field-free region must be made available for spatial encoding for MPI measurements. As a rule, a field-free line (FFL) is used as a field-free region for high resolution and sensitive imaging.

A further application of selection magnetic fields lies in magnetic fluid hyperthermia (MFH), in which regions of a tissue to be treated are heated locally. In this case, a selection magnetic field with a field-free point is preferably used as field-free region in order to be able to locally tightly restrict the heat to be introduced into the tissue to be treated. To this end, the same principle is exploited as for the spatial encoding in MPI imaging. Particles in the vicinity of the field-free region experience a significant change in magnetization, with particles at a distance from the field-free region remaining in magnetic saturation. Magnetization losses of the particles consequently lead to a local increase in temperature.

Patent document WO 2011/021165 A1 describes a magnetic particle imaging (MPI) apparatus, in which a field-free region is generated by means of at least three coil pairs. One embodiment described a Maxwell coil pair which, in combination with coil pairs arranged perpendicular thereto in an XY-plane, generates a field-free line. In the case of appropriate energization of these coil pairs, the field-free line can be rotated or displaced within the field of view (FOV) without physically rotating the coils. Disadvantages of this apparatus include the requirement of many coils and amplifiers for rotating the field-free line, the coupling of the coils among themselves and the driving and closed-loop control, and so only restricted use of the apparatus for hyperthermia is possible.

Patent document WO 2018/013731 A1 discloses an MPI system comprising an electromagnet arrangement which is configured such that it generates a magnetic field with a field-free line. The field-free line can be generated using a magnetic quadrupole and can be converted into a punctiform or ellipsoidal field-free region by means of shim magnets. Furthermore, the shim magnet can be configured such that there can be localized heating and energy input for spatially selective hyperthermia applications. However, disadvantages of this arrangement include the connected load and cooling required for the electromagnetic arrangement and the required rotation of the magnet for the FFL spatial encoding. Fast imaging can only be generated with an n-PI rotation of the magnet, in which the "sinogram" or the totality of the FFL projections is acquired quickly. Electromagnets can only ensure this if sliding contacts are used, but this is technically very complex and susceptible to errors at the powers required.

SUMMARY OF THE INVENTION

The invention provides a magnet arrangement and a method which make it possible to alternate between a selection magnetic field with a field-free point and a field-free line in order to realize in situ MPI imaging at a high frame rate and precise MFH applications. According to the invention, this object is achieved by a magnet arrangement as claimed herein.

The magnet arrangement according to the invention comprises a quadrupole magnet system with at least one quadrupole ring for generating a quadrupole gradient field, the quadrupole magnet system being arranged coaxially with respect to the Maxwell magnet system.

Mathematically, a magnetic field comprises homogeneous components (in the three spatial directions) and higher field terms (in each of the three spatial directions). In general, the latter are referred to as gradients. For the selection magnetic field to be generated, the first field order (i.e., the linear gradients in the three spatial directions) of the magnetic field resulting from the magnet arrangement is of particular interest. To this end, both the zeroth order (homogeneous fields) and the higher orders must disappear/be minimized in the design of the magnet arrangement according to the invention.

A Maxwell magnet system comprises two identical, spaced apart, axially or radially magnetized magnetic rings and generates a Maxwell gradient field of the form $G_{Maxwell}=[-M/2\ 0\ 0;\ 0-M/2\ 0;\ 0\ 0\ M]$, comprising a static field-free point. In this case, the Maxwell gradient field $G_{Maxwell}$ is represented by a gradient matrix. This notation specifies the gradient strength (i.e., the slope/derivative of the magnetic field) for the three spatial directions and the three field directions. In the example of the Maxwell gradient field $G_{Maxwell}$, the gradient strength in the X-direction with the field direction in the X-direction is $-M/2$. The resultant magnetic field at the location X can be calculated by multiplying the gradient matrix by the location vector. In a manner analogous thereto, the quadrupole gradient field generated by the quadrupole magnet system can be represented in the form $G_{Quadrupole}=[-Q\ 0\ 0;\ 0\ Q\ 0;\ 0\ 0\ 0]$.

By superposing the quadrupole gradient field generated by the quadrupole magnet system on the Maxwell gradient field generated by the Maxwell magnet system, it is possible to generate differently shaped field-free regions. Decisive for the shape of the field-free region is the ratio of the Maxwell gradient strengths M (maximum Maxwell gradient strength) and the quadrupole gradient strength Q (maximum quadrupole gradient strength). Thus, in the case of a suitable ratio of the gradient strengths M and Q of the gradient fields $G_{Maxwell}$ and $G_{Quadrupole}$ generated by the Maxwell and quadrupole magnet systems, it is also possible to generate a field-free region with an elongate extent, in particular a field-free line (with the condition Q=M/2), in addition to a field-free point (with the condition Q=0). The direction perpendicular to both the elongate extent of the field-free region and the common Z-axis of the Maxwell magnet system and the quadrupole magnet system is referred to as X'-direction.

This allows the magnet arrangement according to the invention to be used at the same location (in situ), i.e., without having to displace the object, for both high-resolution and sensitive imaging and for magnetic fluid hyperthermia.

Preferably, the ring magnets of the Maxwell magnet system are permanent magnetic rings which are arranged coaxially along a common Z-axis that extends through the sample volume. In practice, these can be realized by discrete magnet segments. The Maxwell ring magnets are magnetized either axially or radially. A cylindrical magnet object is also understood to be a magnetic ring.

Preferably, the ring magnets of the Maxwell magnet system are axially magnetized since axially magnetized magnetic rings are easy to produce. However, it is also possible to use radially magnetized ring magnets.

The quadrupole magnet system is preferably arranged in a plane of symmetry of the Maxwell magnet system. The quadrupole magnet system thus is preferably arranged axially between the two ring magnets of the Maxwell magnet system, level with the isocentre of the Maxwell magnet system. From a radial point of view, the quadrupole magnet system can be located within or outside of the Maxwell magnet system.

The ring magnets of the Maxwell magnet system can be embodied as permanent magnets (Maxwell permanent magnet system) or as electromagnets (Maxwell coil magnet system). In the latter case, a corresponding coil winding can be provided about the Z-axis for the axial magnetization or provision can be made for a winding about the ring for radial magnetization.

Likewise, the quadrupole rings of the quadrupole magnet system can be embodied as permanent magnets or electromagnets. The use of permanent magnets is advantageous in that the power requirements are minimized. Moreover, sliding contacts or long cables can be dispensed with in the case of rotating fields. This facilitates a high frame rate since it is possible to realize a n-PI rotation and hence continuous spatial encoding.

The drive coil for generating the MPI drive field can consist of partial coils or can be realized by a continuous solenoid coil. In addition to exciting the magnetizable nanoparticles, the drive coil can also be used to detect the magnetization response, for example in the case of MPI measurements.

The focus field coil pair generates a homogeneous offset field, for example in the X'-direction, as a result of which the field-free region is displaced in the corresponding direction from its rest position in the centre of the magnet arrangement.

In a preferred embodiment the quadrupole magnet system is rotatably mounted such that it is rotatable about the Z-axis. As a result, it is possible to realize a rotation of the field-free region about the Z-axis, i.e., in the XY-plane. Sliding contacts can be used to realize the rotational movement of the quadrupole magnet system if the quadrupole rings are embodied as electromagnets.

In the case of a particularly preferred embodiment of the magnet arrangement according to the invention, the quadrupole magnet system comprises at least two concentric quadrupole rings which are rotatable relative to one another about the z-axis and which are able to be coupled to one another. By rotating the quadrupole rings relative to one another it is possible to vary the quadrupole gradient strength in one spatial direction. As a result, it is possible to influence the shape of the field-free region.

Preferably, the quadrupole rings are able to be mechanically coupled to one another such that they can be rotated about the Z-axis together. This can define the alignment of the elongate extent of the field-free region. Coupling and common rotation is implemented after the quadrupole rings were rotated relative to one another in order to adjust a corresponding condition for the shape of the field-free region.

As an alternative to quadrupole rings that are rotatable relative to one another, it is also possible to generate different partial quadrupole fields by means of stationary coils and superpose these on one another or on a further partial quadrupole field generated by a quadrupole permanent magnet.

To vary the Maxwell gradient strength provision can be made for the distance between the ring magnets of the Maxwell magnet system to be variable.

As an alternative or in addition thereto, the ring magnets of the Maxwell magnet system can be partly shorted or able to be shorted in soft magnetic fashion. Consequently, the Maxwell gradient strength can be varied by attaching ferromagnetic elements, in particular iron, radially on the outside to the ring magnets or by introducing ferromagnetic elements into the opening of the ring magnets. If Maxwell electromagnets are used, the Maxwell gradient strength can also be adapted by the Maxwell electromagnets themselves.

The focus field coil pair is preferably rotatably mounted such that it is rotatable relative to the Maxwell magnet system about the Z-axis. Consequently, it is possible to select the direction in which the field-free region is intended to be displaced. Here, the focus field should be aligned orthogonal to the elongate extent of the field-free region, i.e., with field direction X', in order to avoid field components in the Y'-direction saturating the field-free region.

In a special embodiment the focus field coil pair is mechanically coupled to the quadrupole magnet system. Then, the focus field coil pair can be rotated together with the quadrupole magnet system.

As an alternative thereto, provision can be made for the focus field coil arrangement to comprise two stationary focus field coil pairs. By superposing the field components of the two focus field coil pairs it is possible to generate a resultant homogeneous magnetic field in the X'-direction, by means of which the field-free region can be displaced in the X'-direction. Preferably, the two focus field coil pairs generate field components that are aligned perpendicular to one another.

The invention also relates to an apparatus for carrying out MPI imaging and/or magnetic fluid hyperthermia which uses magnetic particles and comprises an above-described magnet arrangement.

Moreover, the invention relates to a method for generating a selection magnetic field with a gradient B1 and a field-free region in a sample volume. In this case, a magnetic field of a Maxwell magnet system and a quadrupole field of a quadrupole magnet system arranged coaxially with respect to the Maxwell magnet system are superposed. To this end, use is preferably made of an above-described magnet arrangement.

The Maxwell magnet system generates a magnetic field with a Maxwell gradient field with a gradient strength M while the quadrupole magnet system generates a magnetic field with a quadrupole gradient field with a gradient strength Q. On its own, the Maxwell magnet system generates a field-free point while a quadrupole magnet system on its own generates a field-free line in the Z-direction. The shape of the field-free region is preferably altered by setting the ratio of the quadrupole gradient strength Q of the quadrupole magnet system to the Maxwell gradient strength M of the Maxwell magnet system. Consequently, a field-free region with an elongate extent in the Z-direction arises if the quadrupole gradient strength Q of the quadrupole field is substantially greater than the Maxwell gradient strength M of the Maxwell magnet system (Q>>M). To generate a field-free line in the XY-plane, the gradient strengths of the gradient fields generated by the quadrupole magnet system and by the Maxwell magnet system are chosen such that $Q=M/2$. The quadrupole gradient strength $Q=0$ is chosen in order to generate a field-free point. A degenerate field-free region with an elongate extent in Y' arises for intermediate values of $0<Q<M/2$.

The Maxwell gradient strength is preferably adjusted by varying the distance between the ring magnets of the Maxwell magnet system or by a soft magnetic shorting of the ring magnets. If electromagnets are used in the Maxwell magnet system, the change in the Maxwell gradient strength can be realized by the energization of the electromagnets.

The quadrupole strength is preferably set by aligning two quadrupole rings of the quadrupole magnet system. The alignment of the quadrupole magnet system in relation to a previously defined X-direction determines the alignment of the field-free region in relation to this X-direction. Therefore, the field-free region is rotated in an angular range about a Z'-axis by rotating the quadrupole magnet system in a preferred variant of the method according to the invention. Here, the Z'-axis is aligned parallel to the Z-axis. The angle of attack and hence the direction of the extent of the field-free region (Y'-direction) is therefore realized by the rotation of the quadrupole magnet system.

This method variant is of particular interest for hyperthermia applications. In hyperthermia applications, particles situated in a hyperthermia volume are excited by hyperthermia excitation. The hyperthermia excitation is implemented by an external radiofrequency magnetic field (100 kHz to 10 MHz) that is usually homogenous. If a selection field is used magnetization losses only arise in the regions where the particles experience a significant change in magnetization. In this way there is a local energy influx.

In the case of a selection field gradient with a field-free line, the heating power can be maximized at its intersection by successively turning the field-free region about the Z'-axis. Here, the intersection is chosen such that it is located in a zone to be overheated (target zone). Despite this maximization of the heating power using an FFL to encode the hyperthermia volume this method is linked to significant unsharpness. This is because all particles experiencing a significant change in magnetization due to the hyperthermia excitation contribute to heating.

The minimal hyperthermia volume corresponds to the volume spanned by the FFR and the displacement thereof through the hyperthermia drive field. Moreover, the effect of hyperthermia volume depends on the utilized particles to be excited. To estimate this hyperthermia volume, the minimum hyperthermia volume must be convolved with the point spread function of the particle magnetization at the chosen hyperthermia excitation frequency.

Further, the distribution of heating power and hence heating dose depends in particular on physiological parameters and the concentration distribution in the hypothermia volume of the particles to be excited.

To focus the local distribution of the heating power or to minimize the hyperthermia volume, the use of the FFP mode is of interest for the (magnetic fluid hyperthermia) hyperthermia application. This is because only particles experiencing a significant change in magnetization due to the hyperthermia excitation contribute to heating. When use is made of a hyperthermia drive field with field component in the Z-direction, the deflection of the field-free point due to the hyperthermia coil arrangement, and hence the hyperthermia volume unsharpness, is minimized if the magnet arrangement according to the invention has the maximum gradient strength in the Z-direction. Should the target zone not be located in the region of the Z-axis, the relative position of the Z'-axis and hence the field-free region can be displaced into the target zone in quasi-static fashion, for example by an appropriate control of the focus field coil arrangement.

A protection zone within which there should be no influx of energy either can be excluded by the angular range (FFL mode) or the hyperthermia excitation must be deactivated when sweeping the field-free region of the protection zone.

Preferably, the above-described magnet arrangement and the above-described method are used for MPI imaging and/or for magnetic fluid hyperthermia.

In the hyperthermia application, provision is preferably made, in addition to the drive coil and the focus field coil arrangement, of an RF hyperthermia coil arrangement for the above-described hyperthermia excitation of superparamagnetic iron oxide nanoparticles within the field-free region of the hyperthermia volume. The hyperthermia volume is located within the sample volume but can optionally be chosen to be smaller than the sample volume if use is made of an additional RF hyperthermia coil arrangement.

By way of example, a solenoid coil with a Z field direction is used as RF hyperthermia coil arrangement. A displacement of the field-free region in the Z'-direction is realized by the RF hyperthermia coil arrangement.

Although, in principle, a displacement of the field-free region in the Z'-direction can also be achieved by a focus field coil pair, the focus field coils are not suitable for an excitation of the magnetizable nanoparticles since focus field coils, as a rule, are operated at low frequencies (DC . . . 5 kHz) but higher frequencies (100 kHz to 10 MHz) are needed for the hyperthermia excitation of the magnetizable nanoparticles. It is therefore advantageous to provide a separate RF hyperthermia coil arrangement.

Further advantages of the invention are apparent from the description and the drawings. The aforementioned features and the features mentioned further below can likewise be employed, according to the invention, in each case by themselves or in any desired combination. The embodiments

DETAILED DESCRIPTION

Figure 1:
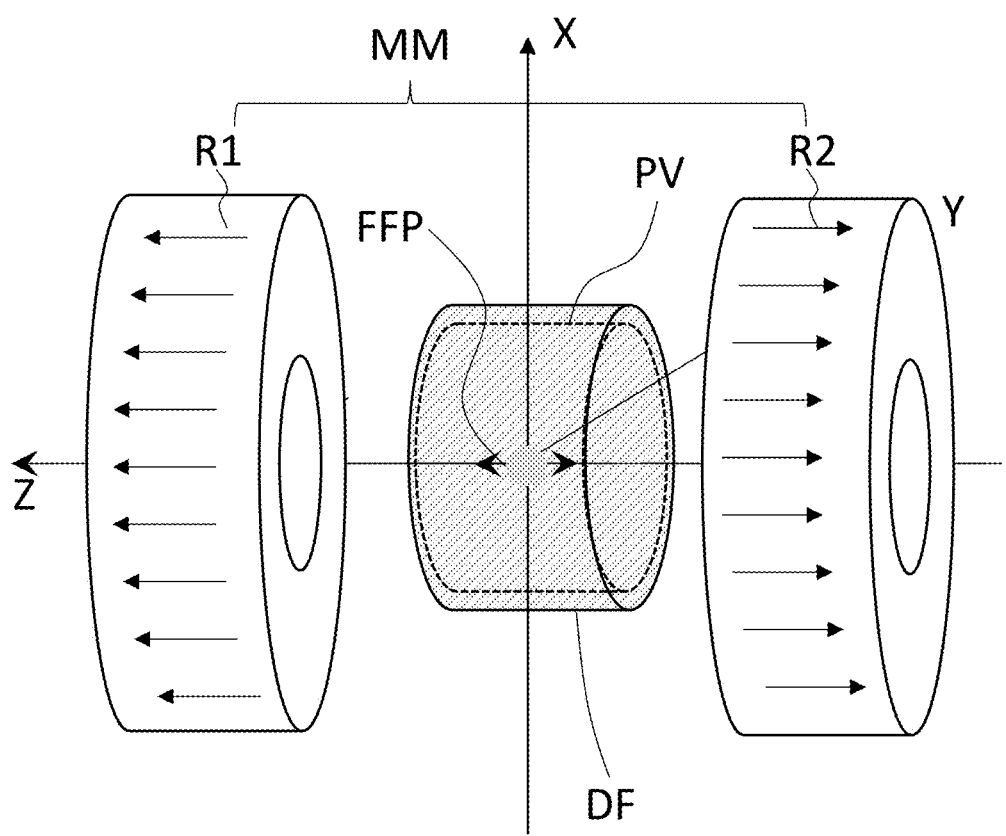
FIG. 1 shows a perspective illustration of a magnet arrangement with a Maxwell magnet pair with axially magnetized ring magnets for generating a static field-free point and a continuously wound drive-field drive coil.

FIG. 1 shows a magnet arrangement with a Maxwell magnet system MM with two axially magnetized ring magnets R1, R2. The ring magnets R1, R2 are arranged coaxially in relation axis Z and at a distance from one another along this axis Z. To excite magnetizable particles, a one-part drive coil DF is located around a sample volume PV. This drive coil DF can also serve to detect a magnetization response generated within the scope of an MPI measurement. The Maxwell magnet system MM generates a rotationally symmetric Maxwell gradient field of gradient strength M with a field-free point FFP in the sample volume PV.

Figure 2:
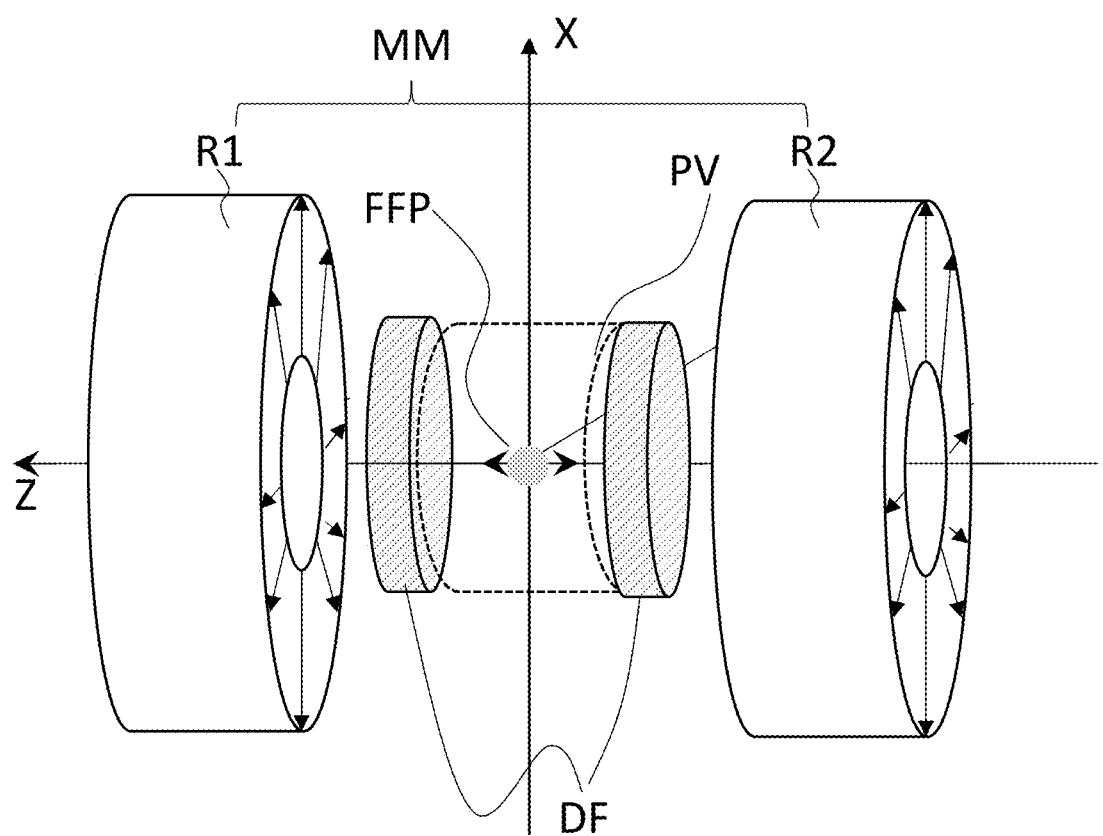
FIG. 2 shows a perspective illustration of a magnet arrangement with a Maxwell magnet pair with radially magnetized ring magnets for generating a static field-free point and a drive-field drive coil consisting of two spaced apart partial coils.

FIG. 2 likewise shows a magnet arrangement with a Maxwell magnet system MM and a drive coil DF for generating a field-free point FFP. In contrast to the magnet arrangement shown in FIG. 1, the magnetic rings R1, R2 of the Maxwell magnet system MM are radially magnetized in FIG. 2. The drive coil DF is in two parts and situated axially outside of the sample volume PV. This facilitates the central arrangement of further components in or around the sample volume PV.

Figure 3:
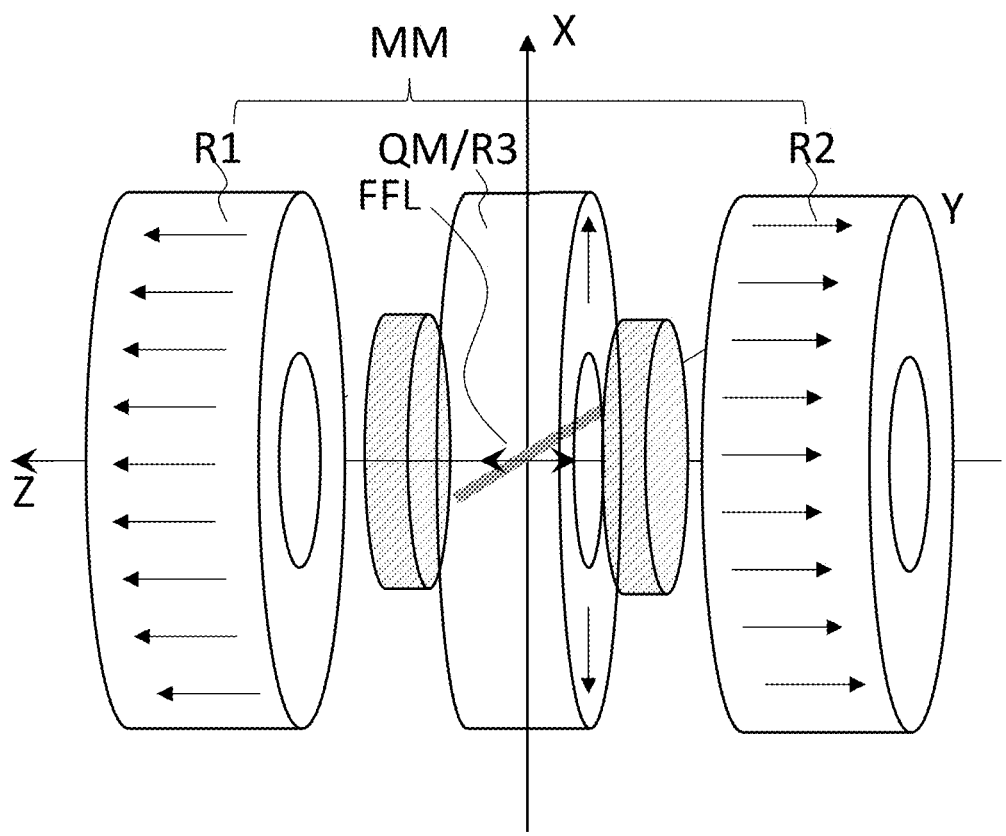
FIG. 3 shows a perspective illustration of a magnet arrangement according to the invention with an axially magnetized Maxwell magnet system and a quadrupole magnet system, and a field-free line generated by the magnet arrangement.
Figure 4:
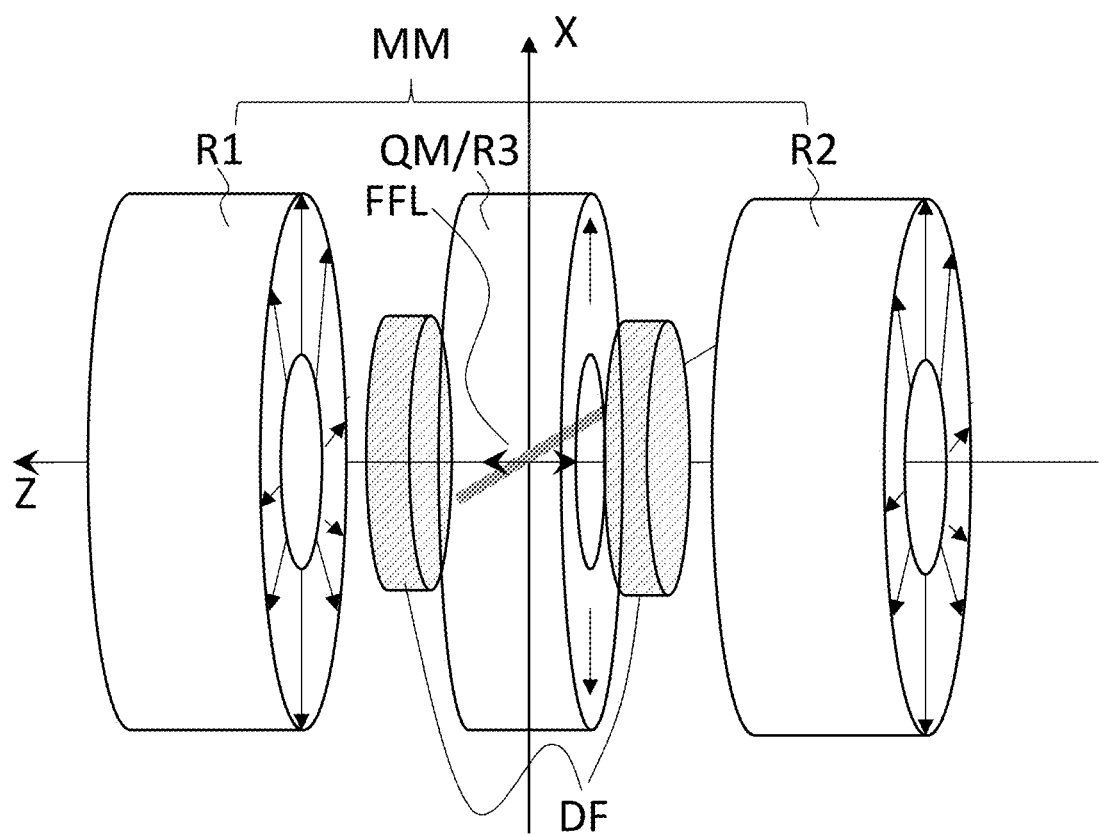
FIG. 4 shows a perspective illustration of a magnet arrangement according to the invention with a radially magnetized Maxwell magnet system and a quadrupole magnet system, and a field-free line generated by the magnet arrangement.

FIG. 3 and FIG. 4 show magnet arrangements according to the invention. According to the invention, a quadrupole magnet system QM is provided in addition to the Maxwell magnet system MM. The gradient B1 of the selection magnetic field according to the invention is therefore composed of a quadrupole gradient field $G_{Quadrupole}$ and a Maxwell gradient field $G_{Maxwell}$. The superposition according to the invention of the Maxwell gradient field $G_{Maxwell}$ and the quadrupole gradient field $G_{Quadrupole}$ allows the generation of a field-free region, the shape of which deviates from the punctiform shape of the field-free point FFP, which is generated by the Maxwell magnet system MM on its own. In exemplary fashion, FIG. 3 and FIG. 4 show a field-free region in the form of a field-free line FFL, the elongate extent of which extends in the Y-direction.

The Maxwell magnet system (Maxwell permanent magnet system or Maxwell coil magnet system) comprises two identical, spaced apart, axially or radially magnetized magnetic rings R1, R2, has a maximum gradient strength M and generates a Maxwell gradient field with a static field-free point FFP, as shown in FIG. 1 and FIG. 2. The Maxwell gradient field generated can be represented by a gradient matrix G:

$$GMM = \begin{bmatrix} -\frac{M}{2} & 0 & 0 \\ 0 & -\frac{M}{2} & 0 \\ 0 & 0 & M \end{bmatrix}.$$

In the embodiments shown in FIG. 3 and FIG. 4, the quadrupole magnet system QM comprises the ring magnet R3, which is arranged coaxially between the magnetic rings R1, R2 of the Maxwell magnet system MM and which is magnetized such that it generates a quadrupole gradient field in the sample volume PV. The Z-axis forms the axis of symmetry, both of the Maxwell magnet system MM and of the quadrupole magnet system QM. The quadrupole magnet system QM is arranged coaxially symmetrically between the magnetized magnetic rings R1, R2 of the Maxwell magnet system MM (which are axially magnetized in FIG. 3 and radially magnetized in FIG. 4).

With the addition (in the axis of symmetry of the Maxwell magnet system MM) of the quadrupole ring R3 which generates a quadrupole gradient field $G_{Quadrupole}$ with the quadrupole gradient strength Q=−M/2 and the gradient matrix $$G_{Quadrupole} = \begin{bmatrix} -Q & 0 & 0 \\ 0 & Q & 0 \\ 0 & 0 & 0 \end{bmatrix},$$

the field-free point FFP from FIG. 1 and FIG. 2 generated by the Maxwell magnet system MM degenerates to an axially true field-free line FFL (see FIG. 3 and FIG. 4) with the gradient matrix $$G = \begin{bmatrix} -M & 0 & 0 \\ 0 & 0 & 0 \\ 0 & 0 & M \end{bmatrix}$$

(along FFL extent in the Y-direction).

The quadrupole ring R3 preferably is a quadrupole permanent magnet system in Halbach dipole configuration (wherein, preferably, the parameter required to calculate the magnetization is k=3) or a quadrupole coil magnet system.

Figure 5:
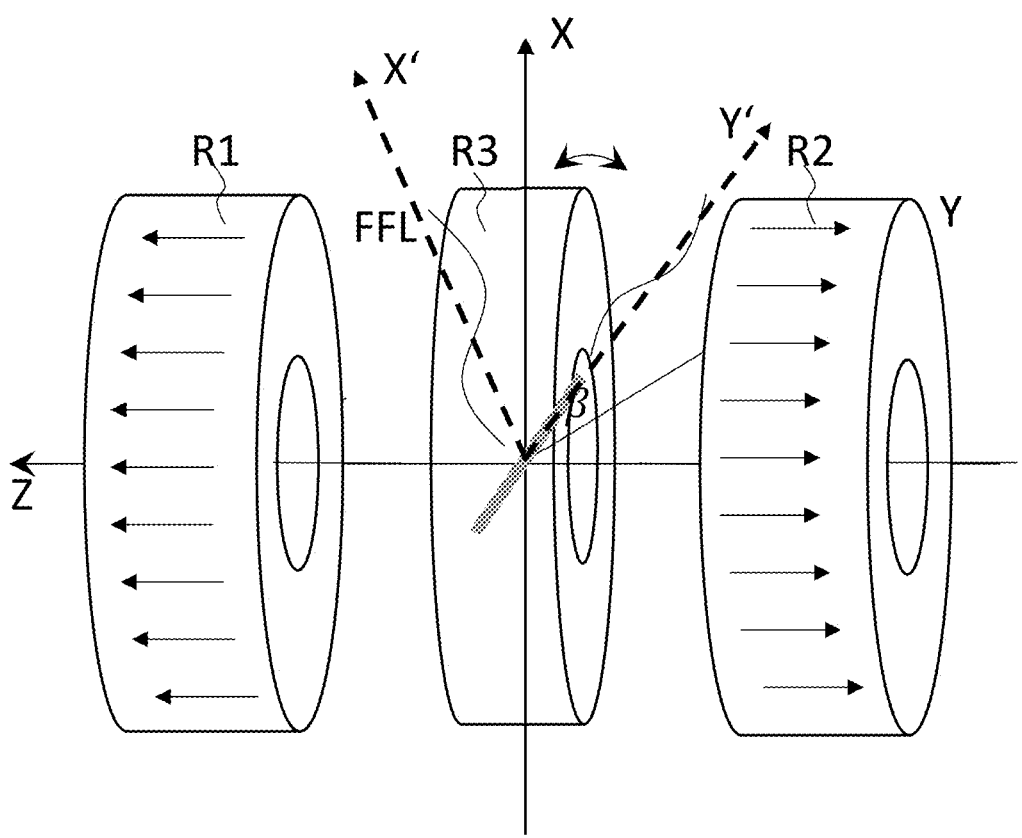
FIG. 5 shows the magnet arrangement of FIG. 3 and a field-free line generated by the magnet arrangement and rotated in the XY-plane.

To be able to record FFL projections over the entire angular range β=0 . . . 180° in the XY-plane, the quadrupole magnet system QM is rotatably mounted such that it can rotate about its axis of symmetry Z. A rotation of the quadrupole magnet system QM about the axis Z through an angle β causes rotation of the field-free line FFL through the angle β in the XY-plane, as illustrated in FIG. 5. The field-free line FFL is now aligned in the Y'-direction (rotating coordinate system X'Y'Z').

The quadrupole magnet system QM can have a plurality of quadrupole rings R3a, R3b, which can be rotated relative to one another. This allows the quadrupole strength Q of the quadrupole gradient field to be varied. FIGS. 6-9 show those magnet arrangements with a quadrupole magnet system QM which each have two quadrupole rings R3a, R3b, with each quadrupole R3a, R3b generating a partial quadrupole field.

In the examples shown, the quadrupole rings R3a, R3b are arranged concentrically in the mirror plane XY and around the isocentre of the Maxwell magnet system MM with its two ring magnets R1, R2.

Figure 6:
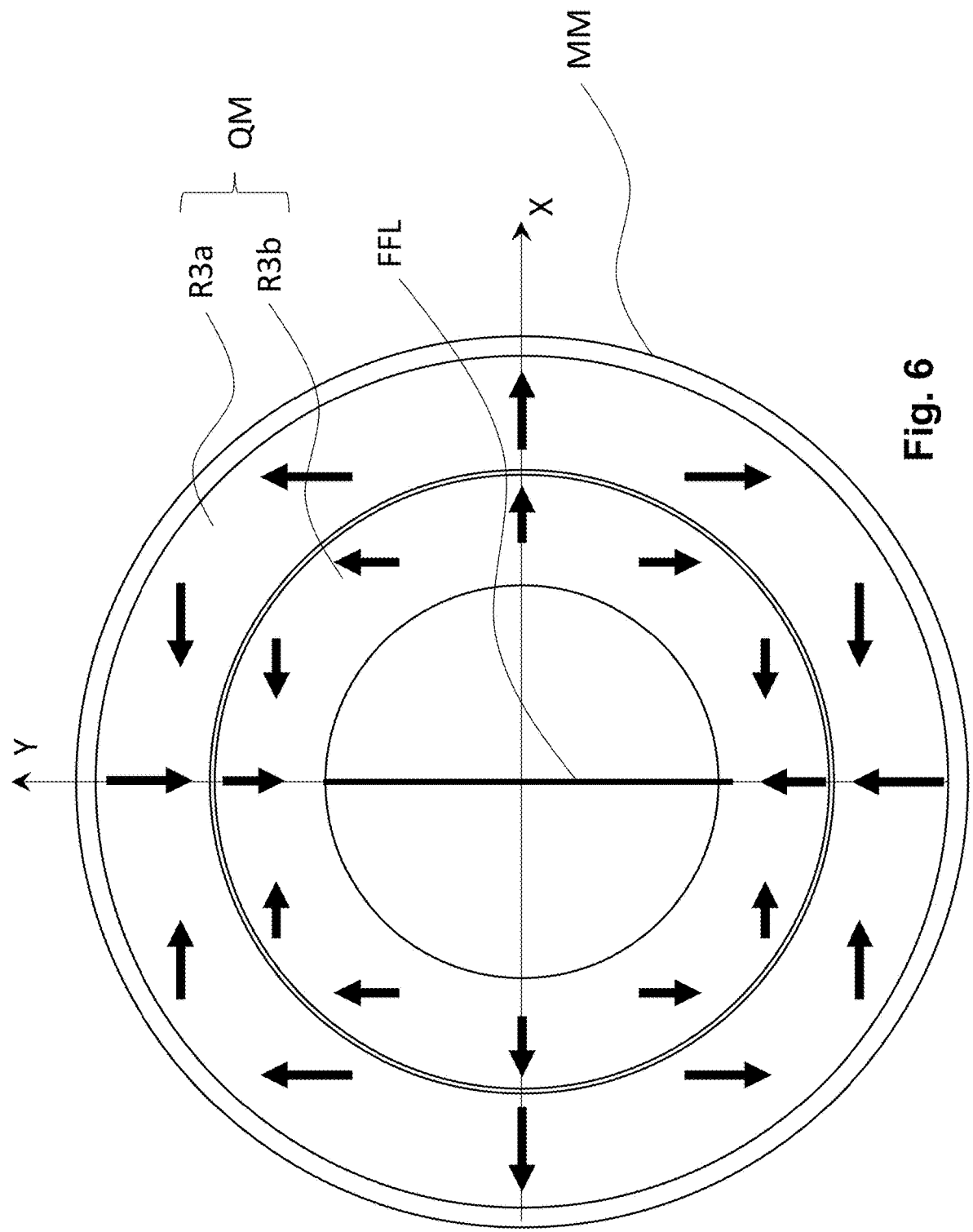
FIG. 6 shows a cross section through a magnet arrangement according to the invention which comprises a quadrupole magnet system with two quadrupole rings (with Q=M/2), wherein the magnetizations of the quadrupole rings are aligned in the same way and a field-free line is generated (FFL mode).
Figure 7:
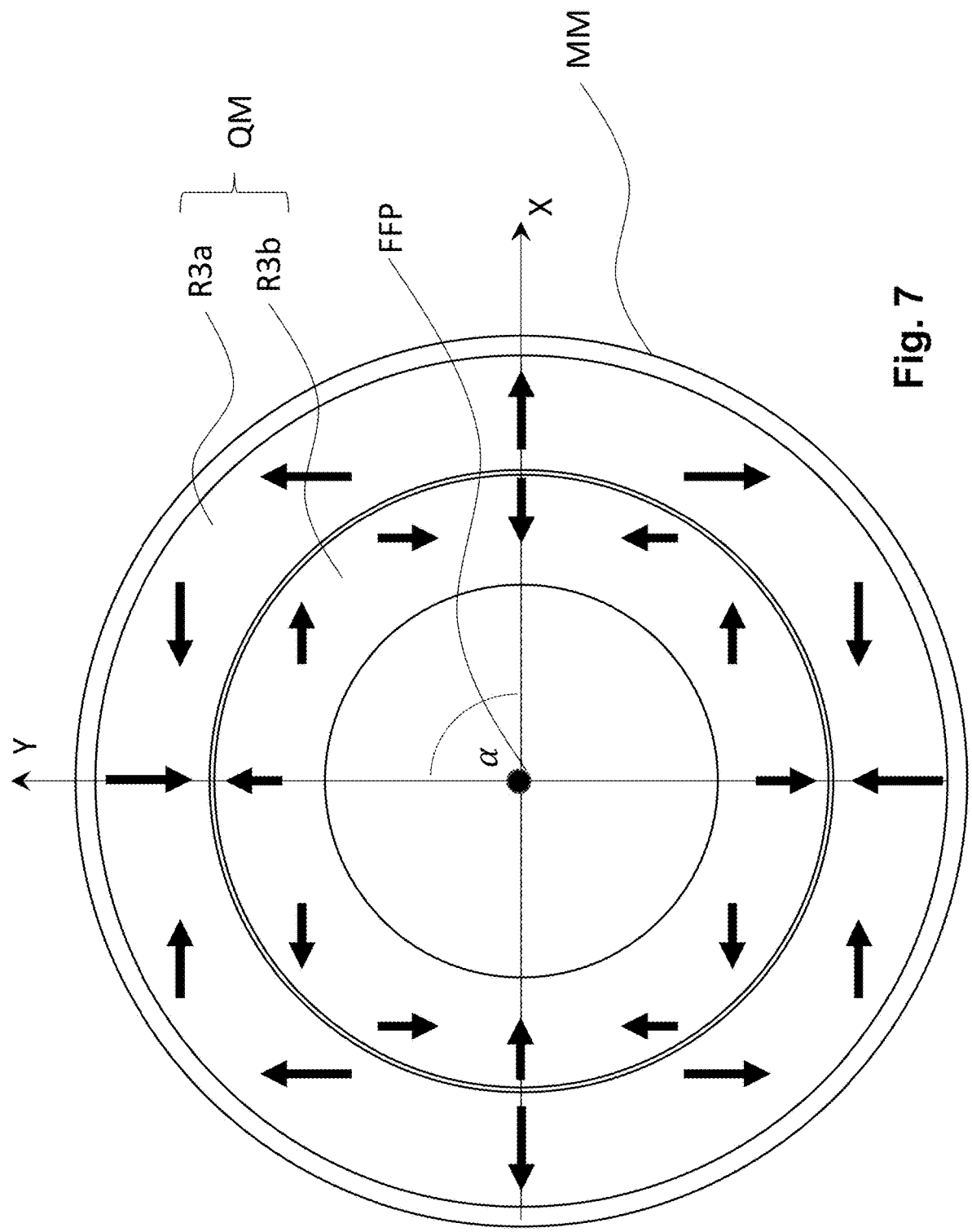
FIG. 7 shows a cross section through a magnet arrangement according to the invention which comprises a quadrupole magnet system with two quadrupole rings (with Q=0), wherein the magnetizations of the quadrupole rings are aligned counter to one another and a field-free point is generated (FFP mode).

In FIG. 6-7, the assumption is made that the partial quadrupole fields of the quadrupole rings R3a, R3b are of equal strength at the centre.

In FIG. 6, the quadrupole rings R3a, R3b are aligned such that their partial quadrupole fields superpose constructively and consequently generate a maximum quadrupole gradient field $G_{Quadrupole}$ with a gradient strength Q. If the condition Q=M/2 is satisfied, a selection magnetic field with a field-free line in the XY-plane arises (FFL mode).

If the quadrupole rings R3, R3 are rotated through α=90° in relation to the arrangement shown in FIG. 6, as shown in FIG. 7, the two partial quadrupole fields of the two quadrupole rings R3a, R3b are aligned counter to one another and cancel one another (Q=0). In this case, a selection magnetic field with a field-free point FFP arises, corresponding to the Maxwell gradient field $G_{Maxwell}$ with a maximum gradient strength M generated by the Maxwell magnet system MM (FFP mode).

Figure 8:
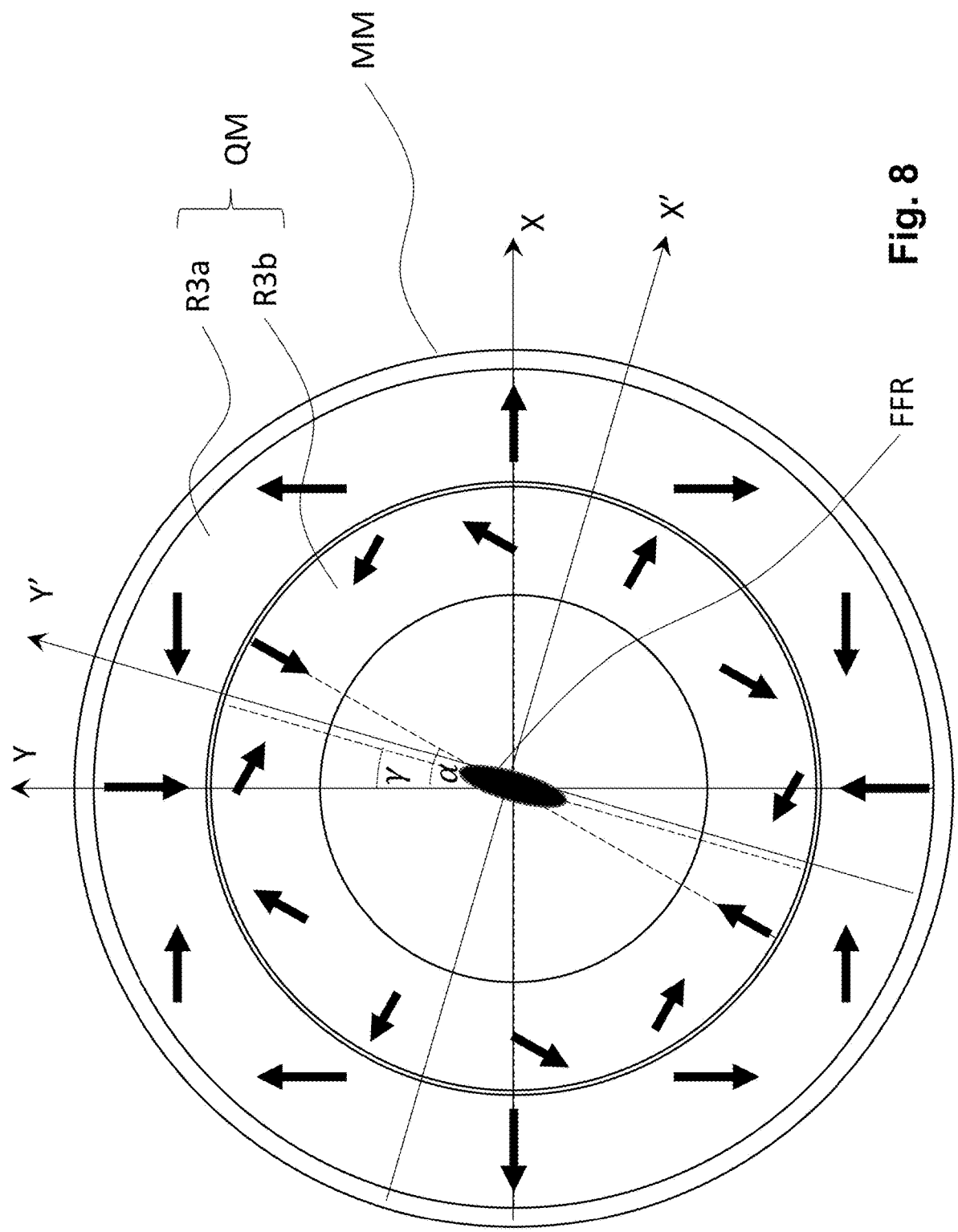
FIG. 8 shows a cross section through a magnet arrangement according to the invention which comprises a quadrupole magnet system with two quadrupole rings (with 0<Q<M/2), wherein the magnetizations of the quadrupole rings are rotated with respect to one another through an angle α and an ellipsoidal field-free region is generated.

If the two quadrupole rings R3a, R3b are rotated against one another through an angle 0<α<90, the partial quadrupole fields are only partly cancelled (0<Q<M/2) and a selection magnetic field with a field-free region FFR in the form of an ellipsoid arises, the elongate extent of which is rotated through the angle γ<α in relation to the Y-direction, as shown in FIG. 8. The quadrupole strength Q can be set continuously by way of the relative rotation of the two quadrupole rings R3a, R3b relative to one another.

Figure 9:
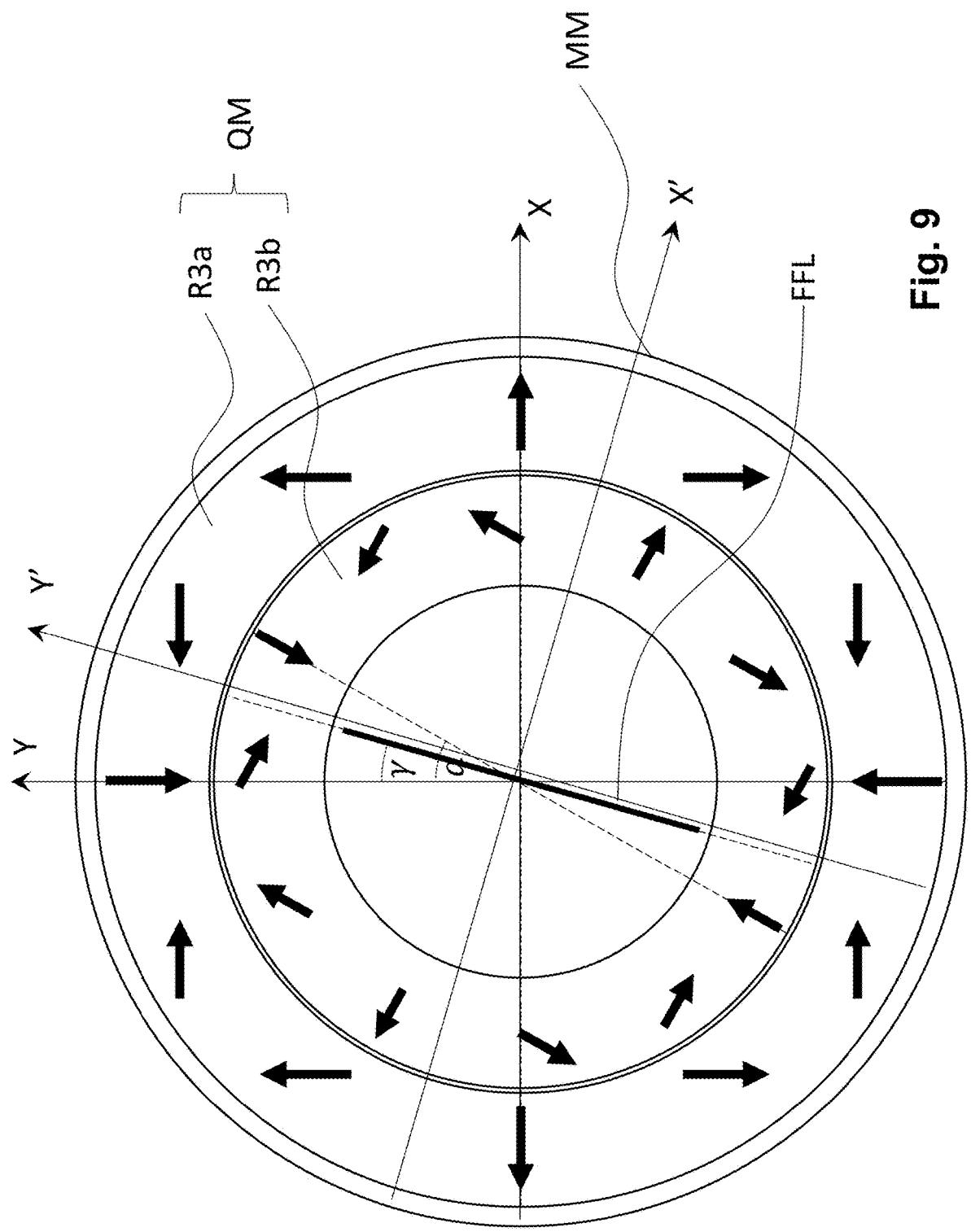
FIG. 9 shows a cross section through a magnet arrangement according to the invention which comprises a quadrupole magnet system with two quadrupole rings (with Q=M/2), wherein the magnetizations of the quadrupole rings are rotated with respect one another through an angle α and a field-free line is generated.

FIG. 9 shows a field-free line FFL that is tilted through the angle γ in relation to the Y-axis. This is achieved by virtue of, firstly, the quadrupole rings R3a, R3b being rotated against one another through the angle α and, at the same time, the Maxwell gradient strength M of the Maxwell magnet system MM being reduced accordingly such that the condition Q=M/2 is satisfied.

What is decisive for the shape of the field-free region is the ratio of the gradient strengths of the gradient fields generated by the Maxwell magnet system and the quadrupole magnet system.

Figure 10:
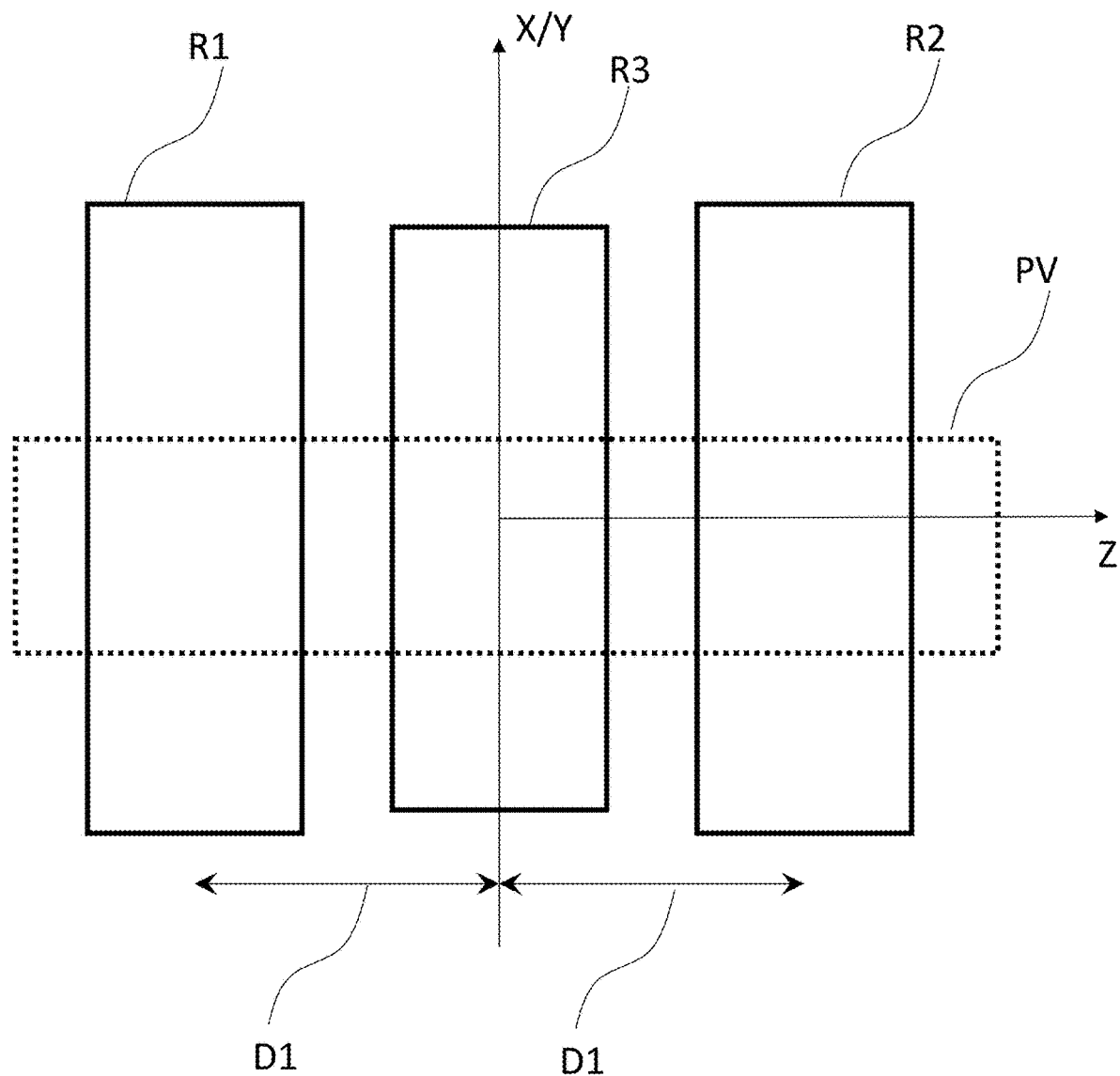
FIG. 10 shows a longitudinal section through a magnet arrangement according to the invention, in which the magnetic rings of the Maxwell magnet system are arranged a distance of 2*D1 with respect to one another.
Figure 11:
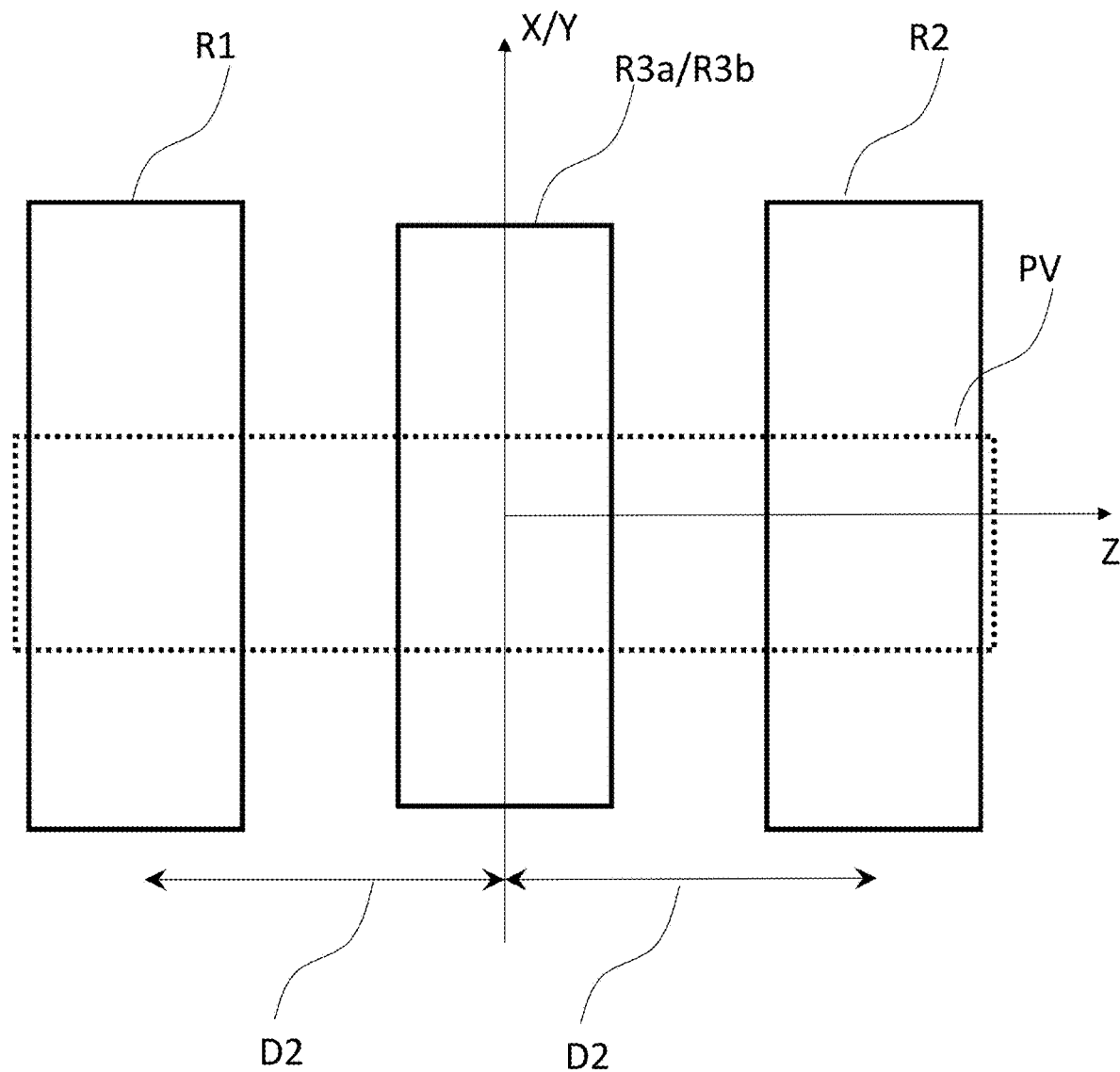
FIG. 11 shows a longitudinal section through a magnet arrangement according to the invention, in which the magnetic rings of the Maxwell magnet system are arranged a distance of 2*D2 with respect to one another.

To change the gradient strength in the FFP mode, it is possible to vary the spacing of the two ring magnets R1, R2 in the case of a Maxwell magnet system with permanent magnets or to vary the current density in the case of a Maxwell magnet system with magnetic coils. FIG. 10 and FIG. 11 show such a variation.

FIG. 10 shows a magnet arrangement with a Maxwell magnet system MM, in which the ring magnets R1, R2 are arranged axially within the sample volume PV at a distance D1 from the isocentre of the magnet arrangement while in FIG. 11 the ring magnets R1, R2 are arranged at a maximum distance from one another (at the edge of the sample volume PV) at a distance D2 from the isocentre of the magnet arrangement. The change in the distance of the ring magnets R1, R2 from the centre of the magnet arrangement changes the resultant Maxwell gradient strength M of the Maxwell magnet system MM.

Figure 12:
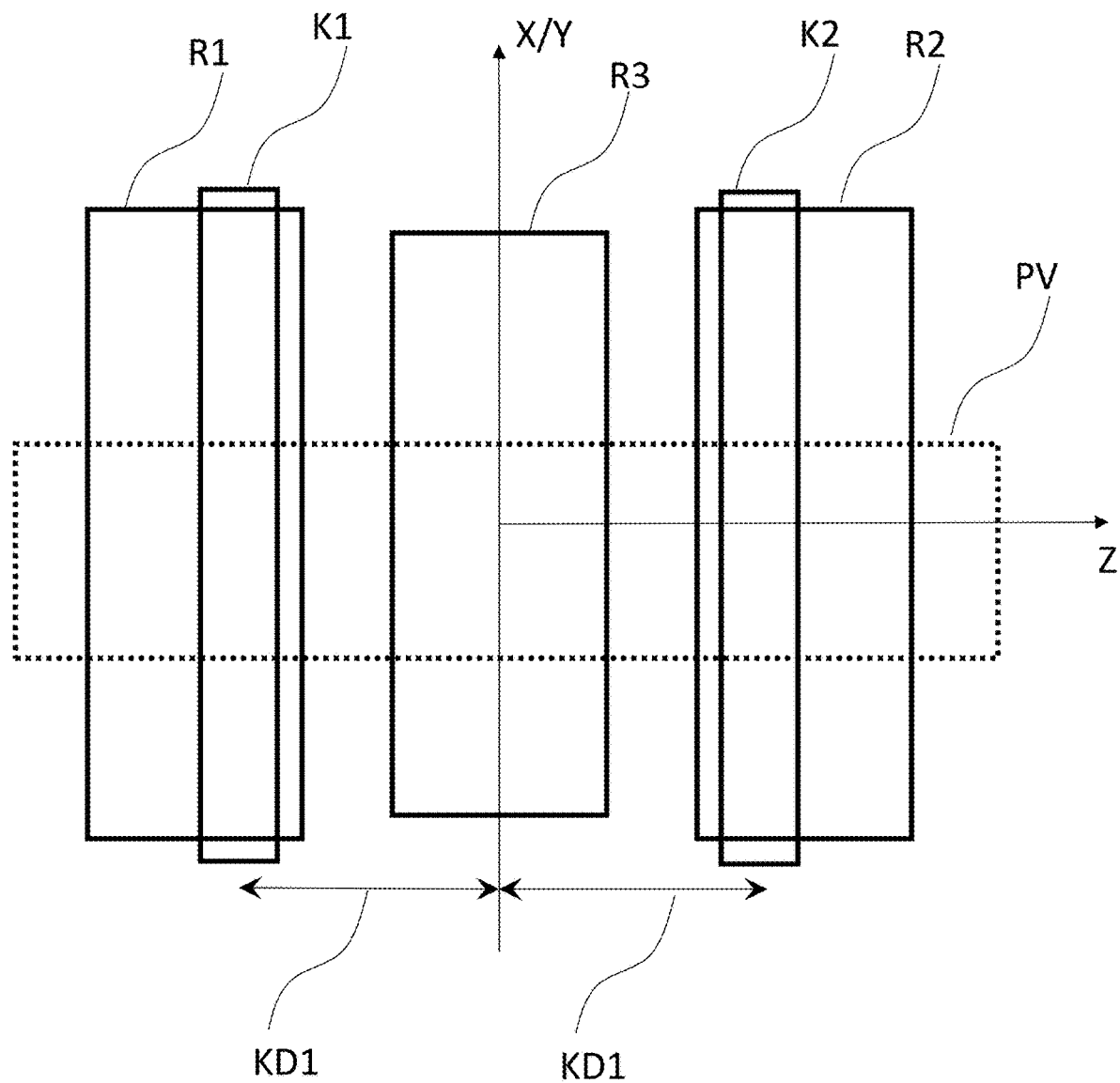
FIG. 12 shows a longitudinal section through a magnet arrangement according to the invention which has soft magnetic cylinder structures in the Maxwell magnet system.

A further option for changing the Maxwell gradient strength M is shown in FIG. 12. In this case, soft magnetic cylinder structures K1, K2 are arranged around the ring magnets R1, R2. Depending on the axial positioning (at a distance of KD1 from the isocentre of the magnet arrangement in FIG. 12) of the soft magnetic cylinder structures K1, K2, the Maxwell gradient strength M of the Maxwell magnet system MM can be influenced to a greater or lesser extent.

To change the Maxwell gradient strength in the FFL mode, the spacing of the two ring magnets R1, R2 can be varied in the case of a Maxwell magnet system MM with permanent magnets as described above or the current density can be varied in the case of a Maxwell magnet system MM with magnetic coils, wherein the requirement Q=−M/2 must be observed. In order to observe the requirement Q=−M/2, the quadrupole gradient strength Q can be realized by the above-described rotation of the two concentrically radially nested quadrupole rings R3a, R3b in the case of a quadrupole permanent magnet system or by an appropriate adaptation of the current density in the case of a quadrupole coil magnet system.

In the case of 0<Q<M/2, the arising field-free region FFR is a flattened ellipsoid with a long extent in the Y'-direction, medium extent in the X'-direction and minimal extent in the Z-direction.

A field-free line FFL in the z-direction arises in the case M=0, Q≠0.

To be able to record projections of the field-free region over the entire field of view at each angle β=0 . . . 180°, the field-free region (to the extent it has an elongate extent) must be displaced orthogonally to its long extent in the XY-plane. This can be realized by focus field coil arrangement FF.

Figure 13:
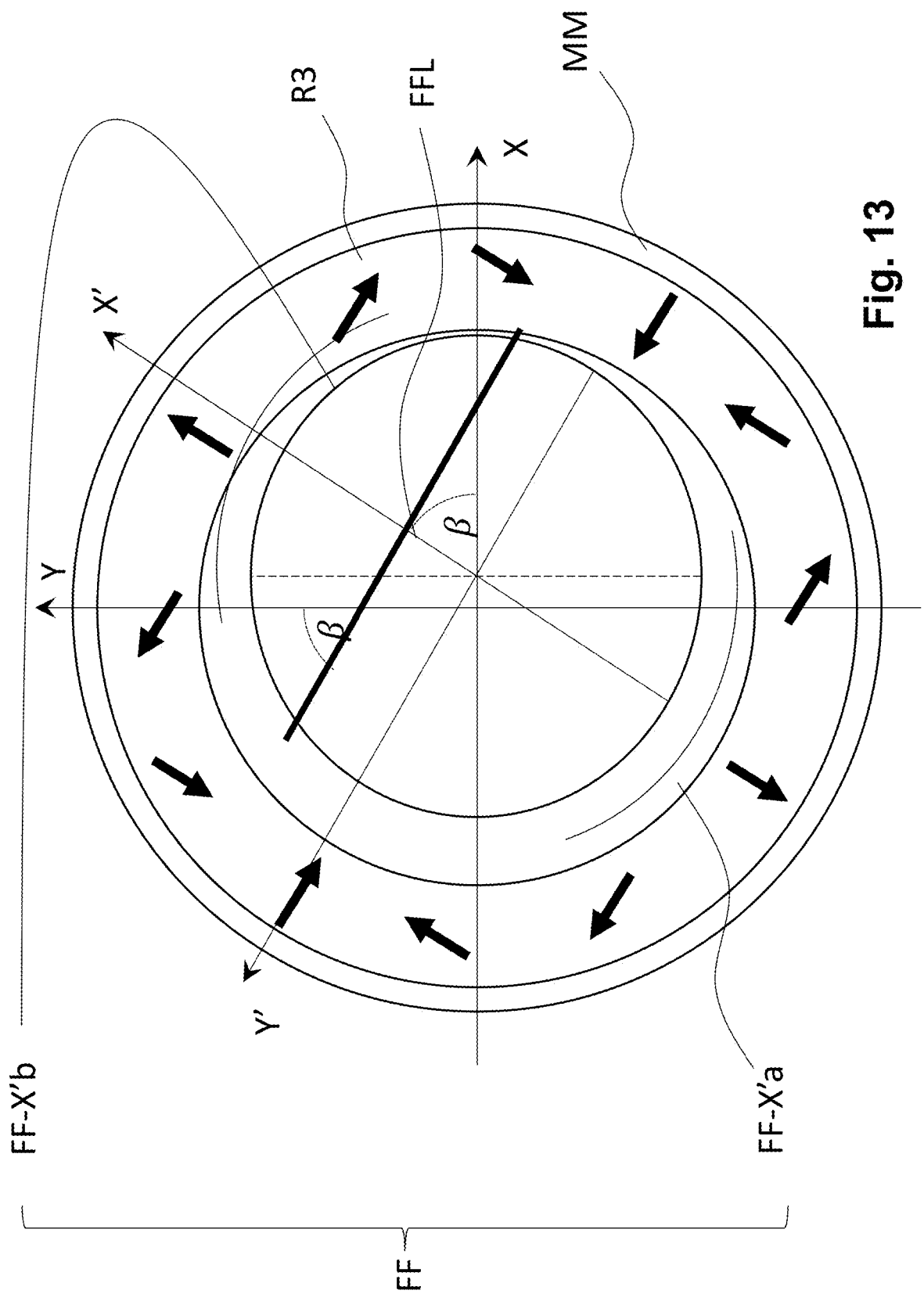
FIG. 13 shows a cross section through a magnet arrangement according to the invention which has a quadrupole magnet system and a rotatable focus field coil pair, which generates a field-free line that is displaced in the X'-direction.

FIG. 13 shows an embodiment in which the focus field coil arrangement FF comprises a focus field coil pair FF-X'a/FF-X'b that is rotatable about the Z-axis. The focus field coil pair FF-X'a/FF-X'b generates a focus field in the X'-direction. This brings about a displacement, for example of a field-free line FFL in the X'-direction. The focus field coil pair FF-X'a/FF-X'b can preferably be mechanically coupled to the quadrupole magnet system such that these can be rotated together. This ensures that the displacement by the focus field coil arrangement FF is implemented perpendicular to the elongate extent of the field-free region (the field-free line FFL in this case).

Figure 14:
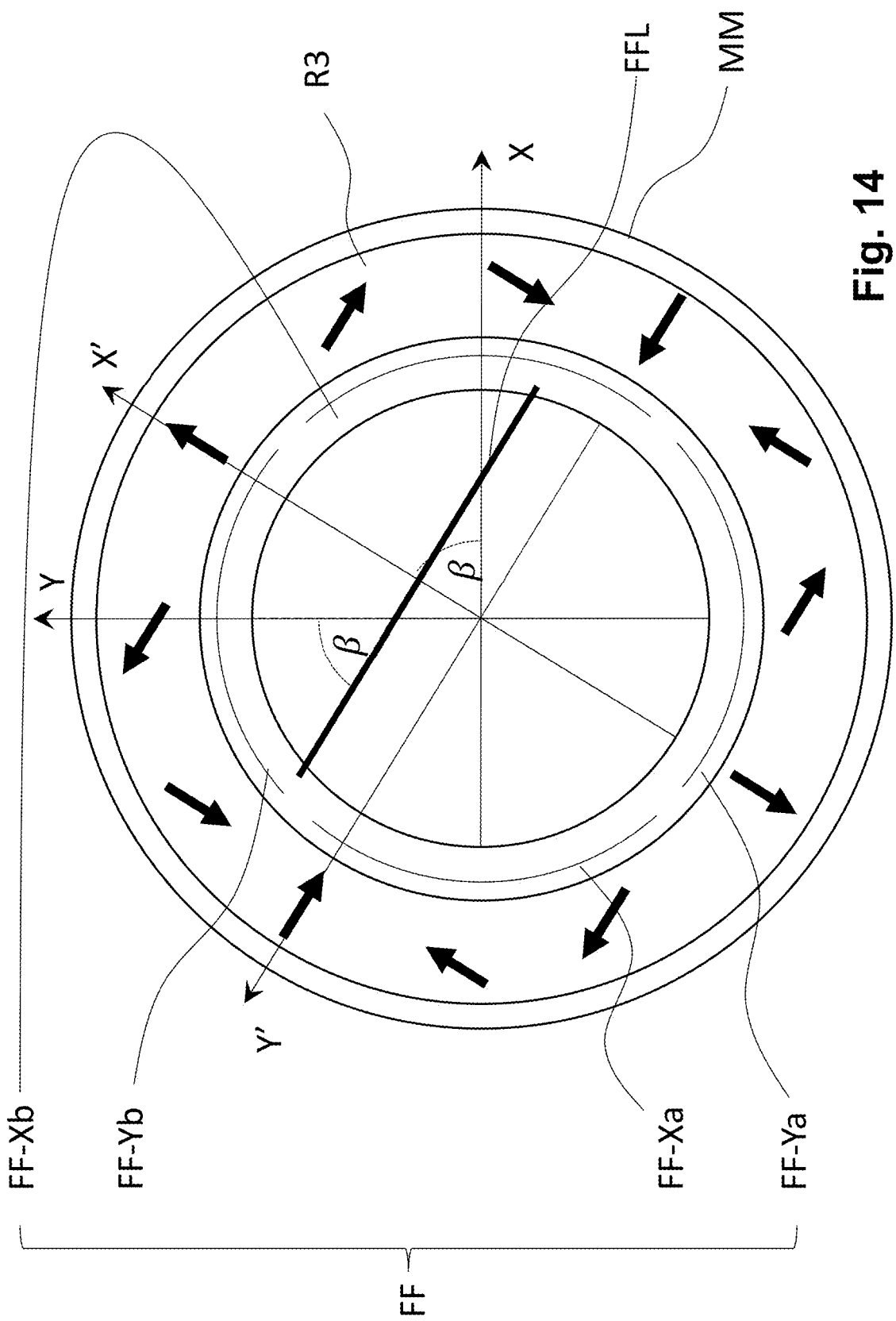
FIG. 14 shows a cross section through a magnet arrangement according to the invention which has a quadrupole magnet system and two stationary focus field coil pairs, which generates a field-free line that is displaced in the X'-direction.

As an alternative to a rotatable focus field coil pair FF-X'a/FF-X'b, the focus field coil arrangement FF may also have a plurality of stationary focus field coil pairs FF-Xa/FF-Xb, FF-Ya/FF-Yb, as shown in FIG. 14. By the superposition of the field components in the X- and Y-direction generated by the two focus field coil pairs FF-Xa/FF-Xb, FF-Ya/FF-Yb, it is possible to generate a resultant magnetic field in the X'-direction. By way of an appropriate control of the coil currents of the focus field coil pairs FF-Xa/FF-Xb, FF-Ya/FF-Yb, it is consequently possible to displace the field-free line from its rest position in the centre in the X'-direction.

Thus, the shape and the alignment of the field-free region can be influenced by the magnet arrangement according to the invention. In particular, it is possible to alternate between an FFL mode, in which a field-free line FFL is generated, and an FFP mode, in which a field-free point is generated.

By means of the magnet arrangement according to the invention it is possible to easily alternate between the FFP mode and the FFL mode. To obtain the FFP mode, the quadrupole magnet system QM must be deactivatable. This can be realized by deactivation of the current in the case of an electromagnet or by an appropriate rotation of the two concentrically radially nested quadrupole rings R3a, R3b in the case of a permanent magnet quadrupole, as shown in FIG. 7.

Alternating between FFP mode and FFL mode facilitates in particular the use of the magnet arrangement according to the invention in different fields of use. Thus, the magnet arrangement according to the invention can be used, for example, both for MPI measurements and for hyperthermia applications.

To excite the magnetizable particles for imaging (e.g., MPI) in the FFL mode, a sufficient amplitude ($|B|>5$ mT) and sufficient frequency (10 kHz$<f_{DF}<$200 kHz) or appropriately high dB/dt must be applied to at least one field component (Bx', By', Bz). This is implemented by the drive coil DF in the case of imaging and by the hyperthermia coil in the case of hyperthermia. In the process, the field-free line FFL is moved from its rest position. To generate particle signal only on a field-free line FFL, a sufficient amplitude ($|B|>5$ mT) and sufficient frequency (10 kHz$<f_{ly}<$200 kHz) or an appropriately high dB/dt must be applied to a field component By' [rotating coordinate system]. In this case, the field-free line FFL remains static in its position ("needle excitation"), i.e., without location smearing by the drive field; only the isoline (MBI) of the field-free line FFL varies its diameter and hence the field-free line FFL pulses.

To measure the particle response, at least one reception coil system must be designed with the sensitivity of at least one field component (Bx', By', Bz) (ideally the same field component as the excitation field component). By way of example, the drive coil DF (transreceive process) or dedicated receiver coil (receive-only process) can be used as receiver coil system.

In the case of a magnetic fluid hyperthermia (MFH) application, an energy influx (energy deposition) in the form of a development of heat should be implemented by losses in the re-magnetization of the hyperthermia particles in a target zone Z1. Using a selection magnetic field allows the hyperthermia volume to be restricted by virtue of the hyperthermia particles outside of the field-free region FFR remaining in saturation, with the hyperthermia particles in the region swept by the field-free region FFR and hyperthermia excitation experiencing a significant change in magnetization. Spatial encoding of the MFH by way of a static selection magnetic field can be used to keep the energy influx by MFH local. However, the sample volume PV may simultaneously also contain regions where there should be no energy deposition where possible (protection zone Z2) but which may contain hyperthermia particles. To excite the magnetizable particles for the hyperthermia, a sufficient amplitude ($|B|>3$ mT) and sufficient frequency (100 kHz$<f_{hyper}<$10 MHz) or appropriately high dB/dt must be applied to at least one field component (Bx, By, Bz).

Figure 15:
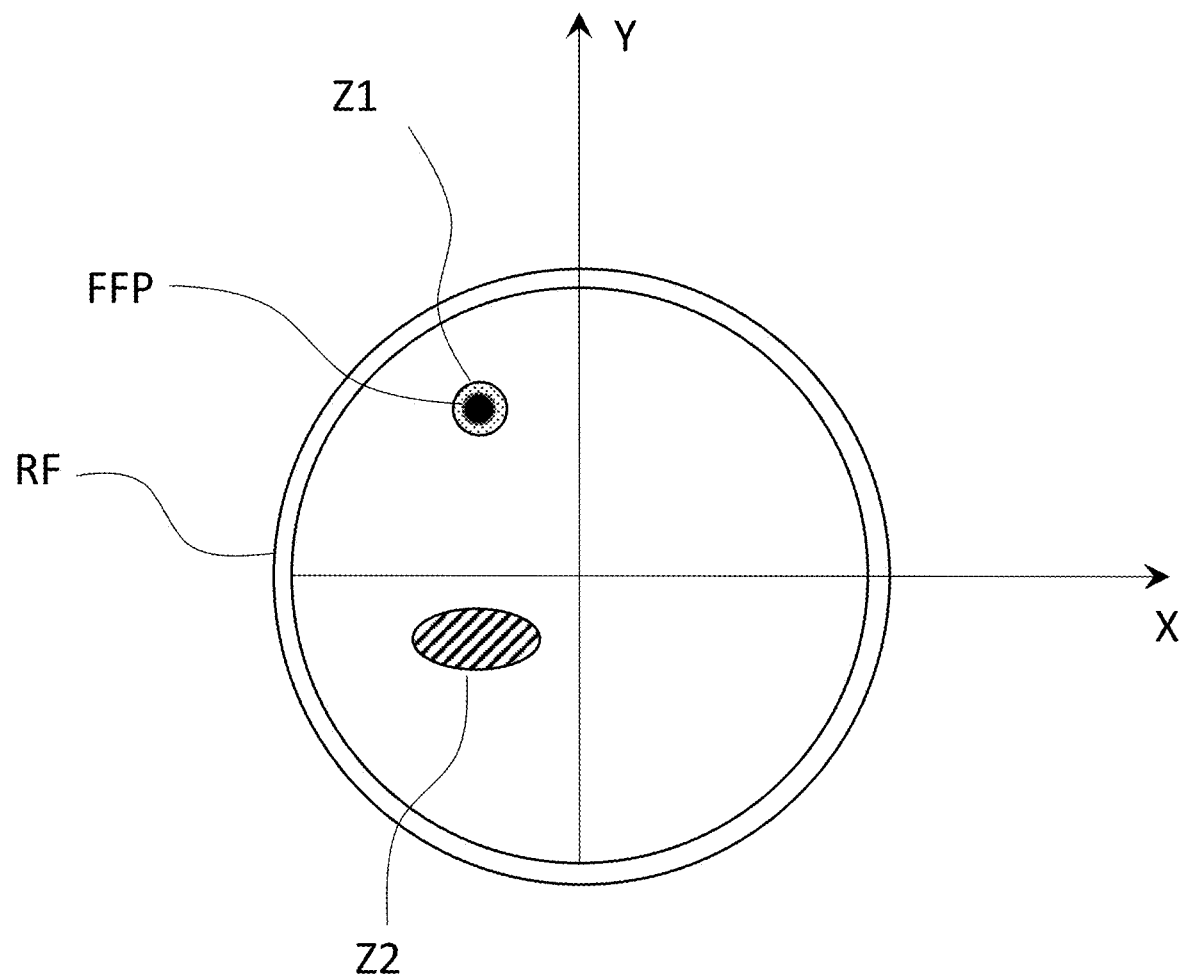
FIG. 15 shows a field-free point generated in the FFP mode in a target zone by the magnet arrangement according to the invention (not shown), and a cross section through a hyperthermia coil.
Figure 16:
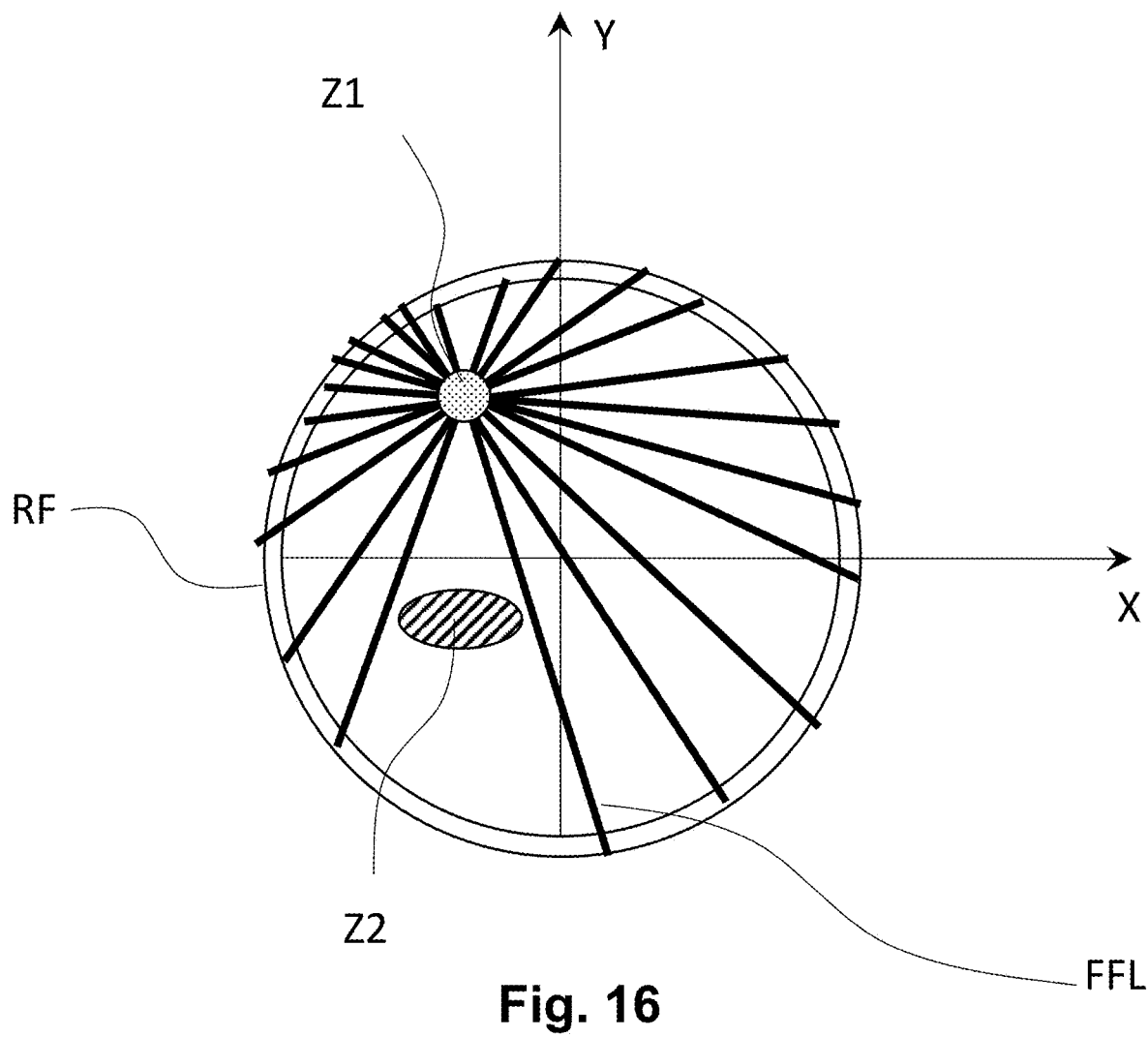
FIG. 16 shows field-free lines which intersect a target zone and were generated in the FFL mode by the magnet arrangement according to the invention (not shown), and a cross section through a hyperthermia coil.

FIG. 15 and FIG. 16 show two different options for implementing a hyperthermia application.

An excitation in the FFP mode with a hyperthermia excitation with field component Bz is advantageous since the focal point of the hyperthermia hence is minimized (excitation along the maximum gradient strength). To this end, the quadrupole magnet system QM is adjusted such that the partial quadrupole fields cancel (Q=0) and a field-free point FFP is generated as field-free region, as described above with reference to FIG. 7 in the case of permanent magnets. By using the focus field coil arrangement FF (either rotatably mounted coil pair which generates a homogeneous field in the Bx' field direction in the rotating coordinate system or two orthogonal securely installed coil pairs, each of which generate a homogeneous field with Bx and By), it is possible to displace the field-free point FFP, and hence the hyperthermia volume, in the XY-plane, as illustrated in FIG. 15.

However, it is also possible to use the magnet arrangement according to the invention in the FFL mode for hyperthermia applications. To this end, a field-free line FFL is generated by means of the Maxwell magnet system MM and the quadrupole magnet system QM. In this case, all particles on the entire field-free line FFL are excited. Consequently, this method is only local to a restricted extent. The field-free line is displaced into the target zone Z1 by means of the focus field coil arrangement FF. The energy dose at the point of rotation of the FFL can be maximized when rotating the field-free line FFL (by rotating the quadrupole magnet system QM) during the hyperthermia excitation and an appropriate adaptation of the field amplitude of the focus field coil arrangement FF (either rotatably mounted coil pair which generates a homogeneous field in the Bx' field direction in the rotating coordinate system or two orthogonal securely installed coil pairs, each of which generate a homogeneous field with Bx and By) (FIG. 16). It is possible to define an angular range which excludes the protection zone Z2 in order to protect the regions contained in the protection zone Z2 from even a brief energy uptake as a result of hyperthermia particles possibly situated therein. Then, the field-free line FFL might only be moved within the defined angular range or there is no hyperthermia excitation of the magnetizable nanoparticles outside of the set angular range (hyperthermia coil is deactivated during the period of time in which the field-free line FFL intersects the protection zone Z2).

In general, it is possible to design the drive coil for generating the MPI drive field in such a way that it can satisfy the above-described functionality of the hyperthermia coil. However, since the frequency for the drive excitation is found in the two-digit kHz range whereas that of the hyperthermia excitation is found in the three-digit kHz range, this would require the use of a double-resonant coil in order to be able to unify both functions. From a technical point of view, it is therefore easier for the two functions to be realized by a separate coil in each case.

Using the magnet arrangement according to the invention it is possible to easily alternate between an axis-true FFP mode and an axis-true FFL mode without unwanted influences on the field gradient. The adjustment of the resultant gradient strength is also facilitated both for a permanent magnet design and for an electromagnet design. Moreover, differently shaped field-free regions are also realizable. This facilitates the use of the magnet arrangement for different applications.

Figure 17:
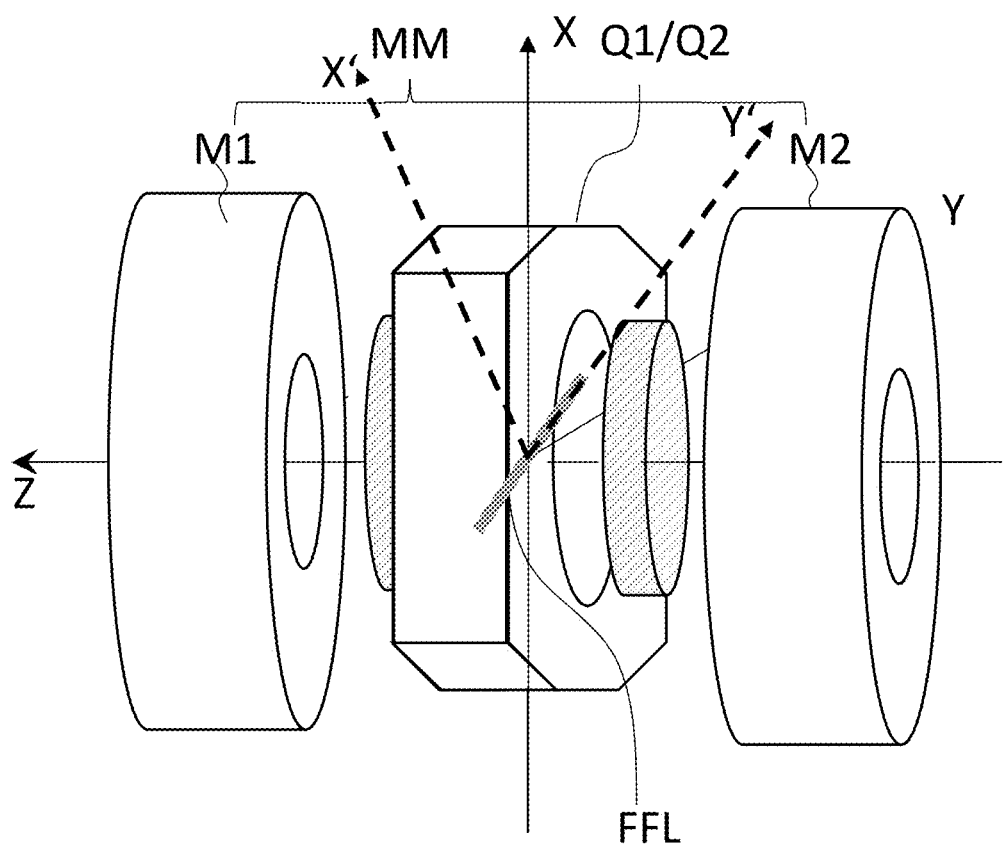
FIG. 17 shows a perspective illustration of a magnet arrangement according to the invention which has a Maxwell electromagnet system and a quadrupole electromagnet system with two quadrupole electromagnets which are rotated with respect to one another through 45°, and a field-free line that was generated by the magnet arrangement and rotated in the XY-plane.

FIG. 17 shows an embodiment of the magnet arrangement according to the invention in which the Maxwell magnet system MM is embodied as a Maxwell electromagnetic coil system and the quadrupole magnet system QM is embodied as a quadrupole electromagnetic coil system with a quadrupole ring (in particular, electromagnetic coils attached in ring-shaped fashion), wherein the quadrupole ring comprises two quadrupole electromagnets Q1, Q2 that are rotated through 45° with respect to one another. The quadrupole magnetic field can be formed by four electromagnetic coils attached in ring-shaped fashion. The field-free line FFL can be rotated electrically if use is made of two independent quadrupole electromagnets (i.e., eight coils), which are rotated through 45° about the Z-axis.

This embodiment of the magnet arrangement according to the invention allows adapting the Maxwell gradient strength M and the quadrupole gradient strength Q merely by way of an appropriate control of the respective electromagnets and a change in the resultant current density. Likewise, this magnet arrangement facilitates a rotation of the field-free region FFR, in particular the field-free line FFL, by way of an appropriate control of the two quadrupole electromagnets Q1, Q2 which are rotated relative to one another. Particularly in combination with stationary focus field coils that are attached orthogonal to one another (in a manner analogous to FIG. 14), the magnetic field arrangement shown in FIG. 17 facilitates rotation of the field-free line FFL without mechanical rotation of the electromagnets Q1, Q2. Hence, this embodiment potentially facilitates higher frame repetition rates since higher FFL rotational speeds that are higher in comparison with mechanical rotations can be achieved in electromagnetic fashion.

The invention claimed is:
1. A magnet arrangement for generating a selection magnetic field with a gradient and a field-free region in a sample volume, the magnet arrangement comprising:
   a Maxwell magnet system with two ring magnets, which are arranged in coaxial fashion and at a distance from one another on a common Z-axis which extends through the sample volume (PV),
   a focus field coil arrangement with at least one focus field coil pair for displacing the field-free region within the sample volume,
   a drive coil for generating an MPI drive field, and
   a quadrupole magnet system with at least one quadrupole ring for generating a quadrupole magnetic field, the quadrupole magnet system being arranged coaxially with respect to the Maxwell magnet system, and being rotatably mounted such that it is rotatable about the Z-axis.

2. The magnet arrangement according to claim 1, wherein the quadrupole magnet system comprises at least two concentric quadrupole rings which are rotatable relative to one another about the Z-axis and which are able to be coupled to one another.

3. The magnet arrangement according to claim 1, wherein the distance between the ring magnets of the Maxwell magnet system is variable.

4. The magnet arrangement according to claim 1, wherein the focus field coil arrangement comprises two stationary focus field coil pairs.

5. An apparatus for carrying out MPI imaging and/or magnetic fluid hyperthermia using magnetic particles with a magnet arrangement according to claim 1.

6. A method for generating a selection magnetic field with a gradient and a field-free region in a sample volume comprising providing a magnet arrangement according to claim 1 and superposing a magnetic field of the Maxwell magnet system and the quadrupole field of the quadrupole magnet system.

7. The method according to claim 6, wherein a shape of the field-free region is altered by adjusting a ratio of a quadrupole gradient strength of the quadrupole magnet system to a gradient strength of the Maxwell magnet system.

8. The method according to claim 6, further comprising adjusting a gradient strength of the Maxwell magnet system by varying a spacing of the ring magnets of the Maxwell magnet system or by shorting the ring magnets in soft magnetic fashion.

9. The method according to claim 6, further comprising rotating the field-free region by rotating the quadrupole magnet system within an angular range about an axis Z'.

10. The method according to claim 9, wherein a relative position of the Z'-axis is displaced into a target zone by a coil arrangement.

11. The method of claim 6 further comprising performing MPI imaging using the superposed magnetic fields in the sample volume.

12. The method of claim 6 further comprising performing magnetic fluid hyperthermia using the superposed magnetic fields in the sample volume.

13. A magnet arrangement for generating a selection magnetic field with a gradient and a field-free region in a sample volume, the magnet arrangement comprising:
- a Maxwell magnet system with two ring magnets, which are arranged in coaxial fashion and at a distance from one another on a common Z-axis which extends through the sample volume (PV), wherein the ring magnets of the Maxwell magnet system are partly shorted in soft magnetic fashion,
- a focus field coil arrangement with at least one focus field coil pair for displacing the field-free region within the sample volume,
- a drive coil for generating an MPI drive field, and
- a quadrupole magnet system with at least one quadrupole ring for generating a quadrupole magnetic field, the quadrupole magnet system being arranged coaxially with respect to the Maxwell magnet system.

14. A magnet arrangement for generating a selection magnetic field with a gradient and a field-free region in a sample volume, the magnet arrangement comprising:
- a Maxwell magnet system with two ring magnets, which are arranged in coaxial fashion and at a distance from one another on a common Z-axis which extends through the sample volume (PV),
- a focus field coil arrangement with at least one focus field coil pair for displacing the field-free region within the sample volume, wherein the focus field coil pair is rotatably mounted such that it is rotatable relative to the Maxwell magnet system about the Z-axis,
- a drive coil for generating an MPI drive field, and
- a quadrupole magnet system with at least one quadrupole ring for generating a quadrupole magnetic field, the quadrupole magnet system being arranged coaxially with respect to the Maxwell magnet system.

\* \* \* \* \*